United States Patent
Caboche (12)

(10) Patent No.: US 6,346,400 B1
(45) Date of Patent: Feb. 12, 2002

(54) PROCESS FOR THE PREPARATION OF A MALTOSE-RICH SYRUP

(75) Inventor: Jean-Jacques Caboche, Drouvin le Marais (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/473,381

(22) Filed: Dec. 28, 1999

(30) Foreign Application Priority Data

Dec. 29, 1998 (FR) .............................. 98 16539

(51) Int. Cl.$^7$ .......................... C12P 19/22; C12P 19/12
(52) U.S. Cl. .............................. 435/95; 435/94; 435/96; 435/101
(58) Field of Search ........................... 435/100, 94, 95, 435/96

(56) References Cited

U.S. PATENT DOCUMENTS

| | | |
|---|---|---|
| 3,708,396 A | 1/1973 | Mitsuhashi et al. |
| 4,294,623 A | 10/1981 | Hidaka et al. |
| 4,429,122 A | 1/1984 | Zupancic |
| 4,487,198 A | 12/1984 | Miyake et al. |
| 4,846,139 A | 7/1989 | Devos et al. |
| 5,141,859 A | 8/1992 | Niimi et al. |
| 5,462,864 A * | 10/1995 | Niimi et al. ................ 435/100 |

FOREIGN PATENT DOCUMENTS

GB     1283571     7/1972

OTHER PUBLICATIONS

Database WPI (XP002114479) JP2092296, Apr. 1990.
Doyle M E et al (XP002114478), vol. 22, n 7, pp. 612–616 Enzyme & Microtech (1998).
Hodge, Cereal Chemistry, 01/48, pp. 19–30.
Wolfrom, Methods in Carbohydrate Chemistry, 1962, pp. 334–335.

* cited by examiner

*Primary Examiner*—Herbert J. Lilling
(74) *Attorney, Agent, or Firm*—Henderson & Sturm LLP

(57) ABSTRACT

The present invention relates to a process for the preparation of a maltose-rich syrup comprising the steps of (a) carrying out liquefaction of a starch milk; (b) carrying out saccharification of the liquefied starch milk in the presence of a β-amylase and at least one debranching enzyme selected from the group comprising pullulanases and isoamylases; (c) carrying out molecular sieving of the liquefied and saccharified starch milk so as to collect a fraction enriched with maltose and a fraction enriched with glucose; and (d) bringing said fraction enriched with maltose into contact with a maltogenic α-amylase with a view to obtaining a maltose-rich syrup.

2 Claims, No Drawings

PROCESS FOR THE PREPARATION OF A MALTOSE-RICH SYRUP

CROSS-REFERENCE TO RELATED APPLICATIONS

Not applicable.

BACKGROUND OF THE INVENTION

1. Field of the Invention

The invention relates to a process for the preparation of a maltose-rich syrup. It also relates to the use of a maltose-rich syrup obtained by the process according to the present invention for the preparation of a maltitol-rich syrup. It also relates to the use of a maltose-rich syrup obtained by the process according to the present invention for the preparation of crystallised maltitol.

2. Description of the Prior Art

Processes by which maltose-rich syrups can be obtained are already well known. These processes include, in particular, the one described by HODGE and co-workers in "Cereal Chemistry" no. 25, pages 19–30, January 1948 and which comprises a step involving the precipitation of limit dextrins by alcoholic solutions, and the one described by WOLFROM and THOMPSON in "Methods in carbohydrate chemistry", 1962, pages 334–335.

Other processes for the preparation of maltose-rich syrups have also been proposed comprising a step involving adsorption of dextrins over carbon (U.S. Pat. No. 4,194,623), a step involving chromatography over zeolites or cationic or anionic resins (FR-A-2,510,581), a step involving ultrafiltration of maltose syrups (U.S. Pat. No. 4,429,122), the combined use of several different enzymes namely an α-amylase, a β-amylase and an isoamylase or a pullulanase (FR-A-2,012,831)

This latter method has numerous advantages over the previous ones. Nevertheless, it suffers from certain disadvantages including, in particular, the fact that the saccharification operations have to be carried out with very low dry matter contents of the order of 20 g/l in order to obtain maximum effectiveness of hydrolysis with enzymes.

The document FR-A-2.000.580 describes a process for the preparation of a syrup with a high maltitol content by hydrogenation of a syrup with a high maltose content which is obtained by liquefaction of a starch milk with a low dry matter content to a dextrose equivalent of less than 2, the product thus obtained being saccharified under the action of specific enzymes.

This process is expensive, has a mediocre yield and gives rise to problems of bacterial contamination and phenomena of retrogradation of the amylose. Moreover, the syrup obtained contains proportions of polymers with degrees of polymerisation (DP, in the description hereinafter) greater than or equal to 4, which are troublesome.

More recently, the document U.S. Pat. No. 5,141,859 proposed a process for the preparation of a syrup with a high maltose content employing two successive saccharification steps. This document advocates, in fact, a process comprising a first saccharification step in the presence of a β-amylase and a subsequent saccharification step in the presence of a maltogenic α-amylase. According to this document, the maltogenic α-amylase is used after the first saccharification step with β-amylase to hydrolyse the oligosaccharides (from DP3 to DP7) and essentially the maltotriose (trisaccharide) to maltose and glucose.

Although the use of maltogenic α-amylase makes it possible, effectively and advantageously, to lower the maltotriose proportion by hydrolysis of the latter to maltose and glucose, it nevertheless has the major disadvantage of generating large quantities of glucose and possibly sorbitol in the event of hydrogenation of the hydrolysates. In fact, a large proportion of glucose originating from the hydrolysis of maltotriose by the maltogenic α-amylase is added to the residual glucose obtained after saccharification of the liquefied starch milk.

These large quantities of glucose, therefore of sorbitol after hydrogenation, make the crystallisation of maltitol more difficult and lead to a reduction in the crystal content, making these crystals ill-suited to certain applications such as, for example, chocolate production.

Moreover, the persistence of free glucose or sorbitol in the maltose or maltitol syrups bring about other disadvantages such as a reduction in the viscosity and equilibrium moisture content of the products in which they are incorporated as sugar substitutes.

In as much as there is a growing interest in products with a very high maltose content, there is a need for considerable research with a view to developing an economical and extremely reliable process for obtaining such products.

DETAILED DESCRIPTION OF THE INVENTION

In an extremely simple and particularly effective manner with regard to all the proposals to date, the Applicant company observed that syrups with a very high maltose content could be prepared by carrying out molecular sieving of a liquefied and saccharified starch milk so as to collect a fraction enriched with maltose and a fraction enriched with glucose, then bringing said fraction enriched with maltose into contact with a maltogenic α-amylase.

The invention proposes, therefore, a process for the preparation of a maltose-rich syrup comprising the successive steps consisting in:

(a) carrying out liquefaction of a starch milk;
(b) carrying out saccharification of the liquefied starch milk in the presence of a β-amylase and at least one debranching enzyme selected from the group comprising pullulanases and isoamylases;
(c) carrying out molecular sieving of the liquefied and saccharified starch milk so as to collect a fraction enriched in maltose and a fraction enriched in glucose;
(d) bringing said fraction enriched with maltose into contact with a maltogenic α-amylase in order to obtain a maltose-rich syrup.

The invention also proposes a process for the preparation of a maltose-rich syrup comprising the successive steps consisting in:

(a) carrying out liquefaction of a starch milk;
(b) carrying out saccharification of the liquefied starch milk in the presence of a β-amylase;
(c) carrying out molecular sieving of the liquefied and saccharified starch milk so as to collect a fraction enriched in maltose and a fraction enriched in glucose;
(d) bringing said fraction enriched in maltose into contact with a maltogenic α-amylase and at least one debranching enzyme selected from the group comprising pullulanases and isoamylases in order to obtain a maltose-rich syrup.

The process for the preparation of a maltose syrup which is the object of the present invention is based in fact on a simple observation which has been neglected hitherto whereby the action of a specific enzyme on a given substrate is effective only if the characteristics as such of the substrate effectively permit the action thereof.

In the present case, an effective action of maltogenic α-amylase may be obtained only on a liquefied and saccharified starch milk having a particular composition, having in particular a bimodal carbohydrate spectrum, namely having, apart from a high maltose and an appreciably high oligosaccharide content, a high glucose content.

The present invention seeks therefore, to ensure that the impurities are in the form of glucose rather than in the form of oligosaccharides, and in particular maltotriose, with a molecular mass close to that of maltose.

The particular bimodal carbohydrate spectrum of the liquefied and saccharified starch milk is obtained according to the process of the invention by carrying out a molecular sieving step on the latter.

The first step of the process according to the invention is inherently known. It consists in liquefying a starch milk of any botanical origin; it may originate from wheat, corn or potato, for example.

Acid is added to this starch milk in the case of so-called acid liquefaction, or an α-amylase is added in the case of enzymatic liquefaction.

In the process according to the invention, it is preferable to carry out controlled hydrolysis of the starch milk so as to obtain a liquefied starch milk with a low degree of conversion. Thus, the conditions of temperature, pH, enzyme and calcium level known to the skilled person are determined in such a way that they make it possible to obtain a DE (dextrose equivalent) of less than 10, preferably less than 6, and more particularly less than 4. Preferably, the liquefaction step is carried out in two sub-steps, the first consisting in heating the starch milk for a few minutes and to a temperature in the range 105° C. to 108° C. in the presence of an α-amylase (TERMAMYL® 120 L type sold by NOVO) and a calcium-based activator, the second consisting in heating the starch milk thus treated to a temperature in the range 95° C. to 100° C. for one to two hours.

Once the liquefaction step has ended, under conditions of dry matter content, pH, enzyme and calcium level that are well known to the skilled person, inhibition of the α-amylase is carried out. This α-amylase inhibition may take place preferably by thermal means by carrying out a thermal shock of a few seconds at a temperature greater than or equal to 130° C. at the outlet of liquefaction.

Saccharification of the liquefied starch milk is then carried out by means of a β-amylase such as that sold by GENENCOR under the name SPEZYME® BBA 1500.

During this step, it is advisable to combine the β-amylase with an enzyme which specifically hydrolyses the α-1,6 bonds of the starch. This addition of a debranching enzyme makes it possible on the one hand to accelerate the hydrolysis reactions without simultaneously accelerating the reversion reactions and, on the other hand, to reduce the quantity of highly branched oligosaccharides normally resistant to the action of maltogenic enzymes.

This addition of debranching enzyme may take place at the time of the addition of β-amylase or at the time of the addition of maltogenic α-amylase.

According to the invention, the debranching enzyme is selected from the group comprising pullulanases and isoamylases. An example of pullulanase is that sold by ABM under the name PULLUZYME® 750 L. An example of isoamylase is that sold by HAYASHIBARA.

Advantageously, the process according to the invention is carried out in the presence of isoamylase, the Applicant company having observed that said isoamylase made it possible to obtain a maltose syrup having a higher maltose content than when pullulanase was used.

In a particular embodiment of the invention, the saccharification step may also be carried out wholly or partially in the presence of fungal α-amylase, for example, SPEZYME® DBA 1500 (sold by GENENCOR) instead of SPEZYME® BBA 1500 (sold by the same company).

At the end of saccharification, it is possible to add a little α-amylase which generally improves the subsequent filtration steps. The quantities and conditions of action of the different enzymes used in the liquefaction and saccharification steps of the starch milk are generally those which are recommended for the hydrolysis of starch and are well known to the skilled person.

Saccharification with β-amylase optionally combined with the debranching enzyme is carried out until the maltose hydrolysate contains at least 75 wt. % of maltose and preferably about 80 wt. % of maltose. It lasts at least 24 hours.

The hydrolysate thus saccharified is then filtered over a precoat filter or by microfiltration over membranes, then demineralised and concentrated.

At this stage of the process according to the invention, the liquefied and saccharified starch milk undergoes molecular sieving in order to collect a fraction enriched with maltose and a fraction enriched with glucose. After this, the fraction enriched with maltose is brought into contact with a maltogenic α-amylase. This latter is advantageously that sold by NOVO under the names Maltogenase® 4000 L and NOVAMYL®.

The molecular sieving step used in the process according to the invention may consist, for example, in a chromatographic separation step or a step involving separation over membranes.

The chromatographic fractionation step is carried out in an inherently known way, batchwise or continuously (simulated mobile bed) over adsorbents of the cationic resin type or over strongly acid zeolites, loaded preferably using alkali or alkaline-earth ions such as calcium or magnesium but more preferably using sodium ions.

Instead of the chromatographic separation step, it is possible, in the process according to the invention, to use a step involving separation by nanofiltration over membranes. Membranes of different pore diameters are produced from numerous polymers and copolymers of the polysulfone, polyamide, polyacrylonitrate, polycarbonate, polyfuran etc. type.

Examples of the use of such membranes are described in particular in the documents U.S. Pat. No. 4,511,654, U.S. Pat. No. 4,429,122 and WO-A-95/10627.

According to an advantageous embodiment of the process according to the invention, the non-maltose part derived from the membranes or from chromatography, comprising the fraction enriched with glucose, is recycled upstream of the saccharification step.

By virtue of the process according to the invention which benefits from the advantages obtained both from the hydrolysis steps used and from the molecular sieving step, it is possible to obtain, with yields greater than 90%, a starch hydrolysate whose maltose content is greater than 95%, and even greater than 98% if an isoamylase is used in the hydrolysis steps.

At this stage of the process according to the invention, it is optionally possible to carry out a crystallisation of the maltose or a catalytic hydrogenation on the hydrolysate (or maltose syrup).

The hydrogenation of such a hydrolysate is carried out according to the rules of the art which lead, for example, to the production of sorbitol from glucose.

It is equally possible to use catalysts based on ruthenium and Raney nickel catalysts for this step. It is preferable, however, to use Raney nickel catalysts which are less expensive.

In practice, 1 wt. % to 10 wt. % of catalyst is used based on the dry matter of the hydrolysate undergoing hydrogenation. Hydrogenation is carried out preferably on a hydrolysate whose dry matter content is in the range 15% to 50%, in practice around 30% to 45%, under a hydrogen pressure in the range 20 bars to 200 bars. It may be carried out continuously or batchwise.

If operations are carried out batchwise, the hydrogen pressure used is generally in the range 30 bars to 60 bars, and the temperature at which hydrogenation takes place is in the range 100° C. to 150° C. It is also important to maintain the pH of the hydrogenation medium by adding soda or sodium carbonate, for example, but without exceeding a pH of 9.0. This method of operating makes it possible to avoid the appearance of cracking or isomerisation products.

The reaction is terminated when the reducing sugar content of the reaction medium has become less than 1%, preferably less than 0.5% and more particularly less than 0.1%.

After the reaction medium has been cooled, the catalyst is removed by filtration and the maltitol syrup thus obtained is demineralised over cationic and anionic resins. At this stage, the syrups contain at least 93% maltitol.

The maltitol syrup obtained in the preceding hydrogenation step may then undergo a crystallisation step in order to obtain crystallised maltitol.

According to a preferred embodiment according to the invention, the maltitol syrup obtained in the preceding hydrogenation step is used, the succession of following steps consisting in:

concentrating the maltitol syrup;

crystallising and separating the maltitol crystals formed;

carrying out molecular sieving on the crystallisation mother liquors and, in particular, chromatographic fractionation so as to obtain a maltitol-rich fraction and a maltitol-poor fraction;

recycling the maltitol-rich fraction upstream of the crystallisation step;

optionally carrying out acid hydrolysis and/or enzymatic hydrolysis on the maltitol-poor fraction using, for example, an immobilised or non-immobilised amyloglucosidase;

optionally carrying out hydrogenation of said hydrolysed maltitol-poor fraction in order to obtain a sorbitol syrup.

Surprisingly and unexpectedly, the use according to the invention of a maltose-rich syrup for the preparation of crystallised maltitol makes it possible to reduce very substantially (up to 80% compared with a conventional process) the quantities of mother liquors (i.e. the maltitol-poor fraction) produced during the molecular sieving step downstream of the crystallisation step.

Other features and advantages of the invention will become clear on reading the examples that follow. They are given here, however, only by way of non-limiting example.

EXAMPLE 1

A starch milk with a dry matter content of 31% is liquefied in the conventional way using 0.2% TERMAMYL® 120 L (α-amylase sold by NOVO) at a pH of 5.7 to 6.5 to a DE slightly below 4.

The reaction medium is then heated for a few seconds to 140° C. in order to inhibit the α-amylase, then the pH is adjusted to between 5 and 5.5 and the temperature to 55° C.

Saccharification is carried out to a dry matter content of 25% or slightly below, in the presence of pullulanase (PULLUZYME® 750 L sold by ABM) and β-amylase (SPEZYME® BBA sold by GENENCOR) in respective amounts of 0.1% and 0.05% based on dry matter.

Saccharification, which lasts about 48 hours, gives a hydrolysate having the following composition. DP1: 1.4%, DP2: 82.4%, DP3: 13.2%, DP4 and above: 2.6%.

The hydrolysate then undergoes conventional purification by filtration, bleaching and demineralisation and is then concentrated to about 20% of dry matter and adjusted to a pH of 5.5.

A step involving the continuous chromatography of the maltose hydrolysate thus obtained is carried out in the following manner.

Four columns of a litre of resin PCR 732 in the sodium form thermostated to 75° C. are assembled in series and fed continuously with the maltose hydrolysate brought to a dry matter content of 60 wt. %, at a flow rate of 110 ml/h.

The fractions enriched with maltose having the following composition are recovered at the outlet of the column:

DP1: 1.5%, DP2: 94%, DP3: 4.5%.

The chromatographic maltose yield is 91.5%.

These fractions are concentrated to about 20% of dry matter and adjusted to a pH of 5.5 then brought into contact with a maltogenic α-amylase (Maltogenase® 4000 L sold by NOVO) in a quantity of 0.3% based on dry matter. The composition of the maltose syrup obtained is as follows: DP1: 4%, DP2: 95.5%, DP3: 0.5%.

EXAMPLE 2

The maltose syrup obtained in example 1 above undergoes a maltose crystallisation step in the following manner. A maltose solution with a dry matter content of 75 wt. % is prepared at a temperature of 75° C. The maltose solution is seeded with 5 wt. % of maltose crystal seeds and the solution is cooled from 75° C. to 40° C. at a rate of 0.5° C. per hour whilst agitating the solution at 50 rpm in a double-walled crystalliser.

At the end of crystallisation, the crystals are separated from the mother liquor using a conventional centrifuge.

The crystallisation yield is 50 wt. % expressed in weight of crystallised maltose based on the starting weight of maltose. The maltose purity of the crystals recovered is 97.5% based on dry matter. The water content is 5%.

EXAMPLE 3

The maltose syrup obtained from example 1 is demineralised then hydrogenated under the following conditions:

| | |
|---|---|
| Dry matter: | 40% |
| Temperature: | 115° C. |
| Amount of catalyst: | 5 wt. %/dry matter |
| $H_2$ pressure: | 50 bars |

The reaction is terminated when the reducing sugars are less than 0.3%. The medium is then filtered, demineralised and concentrated to 85% of dry matter; its composition is:

| | |
|---|---|
| Sorbitol: | 5.5% |
| Maltitol: | 94.0% |
| Higher hydrogenated products: | 0.5% |

The crystallisation step is then carried out by cooling from 75° C. to 25° C. at a rate of 0.5° C./hour under slow agitation, with inoculation with 6 wt. %/dry matter of crystallised maltitol with a particle size in the range 200 μm to 250 μm.

After centrifuging, the crystals are dried and have a content of 99.7%; the mother liquors are adjusted to 60% dry matter and chromatographed.

Four columns of one litre of resin PCR 732 in the calcium form, thermostated to 85° C. are assembled in series and fed continuously at a rate of 120 ml/h. The maltitol yield is 90.7% and the rich fraction (maltitol-rich fraction) has the following composition: sorbitol 4.5%; maltitol 95%; higher hydrogenated products: 0.5%.

The maltitol-poor fraction containing 53.5% of sorbitol, 42.5% of maltitol and 4% of higher hydrogenated products then undergoes an acid hydrolysis step.

Hydrolysis of the maltitol-poor fraction is carried out continuously over a cation exchange resin of the Purolite C145 type in the H' form placed in a column thermostated to 115° C.; by feeding the column at 1 bv/h with the solution concentrated to 40%, the following composition is obtained: sorbitol: 70.5%; maltitol: 12.3%; higher products: 0.4%, glucose: 16.8%.

This solution is then demineralised and hydrogenated under the following conditions:

| | |
|---|---|
| dry matter: | 40% |
| temperature: | 135° C. |

-continued

| | |
|---|---|
| amount of catalyst: | 5 wt. %/dry matter |
| hydrogen pressure: | 50 bars. | until a free reducing sugar content of less than 0.1% is obtained.

What is claimed is:

1. A process for the preparation of a maltose-rich syrup comprising the successive steps of:

(a) carrying out liquefaction of a starch milk;

(b) carrying out saccharification of the liquefied starch milk in the presence of a β-amylase and at least one debranching enzyme selected from the group comprising pullulanases and isoamylases;

(c) carrying out molecular sieving of the liquefied and saccharified starch milk so as to collect a fraction enriched in maltose and a fraction enriched in glucose;

(d) bringing said fraction enriched with maltose into contact with a maltogenic α-amylase in order to obtain a maltose-rich syrup.

2. Process for the preparation of a maltose-rich syrup comprising the successive steps of:

(a) carrying out liquefaction of a starch milk;

(b) carrying out saccharification of the liquefied starch milk in the presence of a β-amylase;

(c) carrying out molecular sieving of the liquefied and saccharified starch milk so as to collect a fraction enriched in maltose and a fraction enriched in glucose;

(d) bringing said fraction enriched with maltose into contact with a maltogenic α-amylase and at least one debranching enzyme selected from the group comprising pullulanases and isoamylases in order to obtain a maltose-rich syrup.

* * * * *